US009080214B2

(12) United States Patent
Lavedan et al.

(10) Patent No.: US 9,080,214 B2
(45) Date of Patent: *Jul. 14, 2015

(54) GENETIC MARKERS FOR EFFICACY OF ILOPERIDONE IN THE TREATMENT OF PSYCHOTIC SYMPTOMS

(75) Inventors: Christian Lavedan, Potomac, MD (US); Simona Volpi, Derwood, MD (US); Louis Licamele, Gaithersburg, MD (US); Mihael H. Polymeropoulos, Potomac, MD (US)

(73) Assignee: Vanda Pharmaceuticals, Inc., Washington, DC (US)

(*) Notice: Subject to any disclaimer, the term of this patent is extended or adjusted under 35 U.S.C. 154(b) by 19 days.

This patent is subject to a terminal disclaimer.

(21) Appl. No.: 12/600,036

(22) PCT Filed: May 17, 2008

(86) PCT No.: PCT/US2008/064027
§ 371 (c)(1),
(2), (4) Date: Nov. 13, 2009

(87) PCT Pub. No.: WO2008/144599
PCT Pub. Date: Nov. 27, 2008

(65) Prior Publication Data
US 2011/0021566 A1 Jan. 27, 2011

Related U.S. Application Data

(60) Provisional application No. 60/939,033, filed on May 18, 2007.

(51) Int. Cl.
C07H 21/04 (2006.01)
C12Q 1/68 (2006.01)

(52) U.S. Cl.
CPC ........ C12Q 1/6883 (2013.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS 5,474,796 A 12/1995 Brennan
2006/0073506 A1* 4/2006 Christians et al. ............... 435/6

FOREIGN PATENT DOCUMENTS

| WO | 03/054226 A2 | 7/2003 |
| WO | 2006/039663 A2 | 4/2006 |
| WO | 2009036056 A1 | 3/2009 |

OTHER PUBLICATIONS

Tacher et al. (J. of Heredity, vol. 96, No. 7, pp. 812-816, 2005).*
Ioannidis (Nature Genetics, vol. 29, pp. 306-309, Nov. 2001).*
Hirschhorn et al. (Genetics in Medicine. vol. 4, No. 2, pp. 45-61, Mar. 2002).*
Lavedan et al. Molecular Psychiatry, vol. 14, pp. 804-819, 2009.*
European Patent Office, Office Action for Application Serial No. 08755809.4 dated Mar. 25, 2010, 8 pages.
Quirin, K., International Search Report for Patent Cooperation Treaty International Application No. PCT/US2008/064027, filed May 17, 2008, issued Nov. 25, 2008 by European Patent Office as International Search Authority.
Jain, K.K., "An assessment of iloperidone for the treatment of schizophrenia," Expert Opinion on Investigational Drugs, 2000, Ashley Publications Ltd., London, GB, vol. 9 No. 12, pp. 2935-2943.
Albers, L.J. et al., "Iloperidone: a new benzisoxazole atypical antipsychotic drug. Is it novel enough to impact the crowded atypical antipsychotic market?" Expert Opinion on Investigational Drugs, 2008 Informa Healthcare UK Ltd., vol. 17 No. 1, Jan. 2008, pp. 61-75.
Pickard, B.S. et al., "Disruption of a Brain Transcription Factor, NPAS3, Is Associated With Schizophrenia and Learning Disability," American Journal of Medical Genetics, vol. 136B No. 1, Jul. 2005, pp. 26-32.
Kamnasaran, D. et al., "Disruption of the neuronal PAS3 gene in a family affected with schizophrenia," Journal of Medical Genetics, vol. 40 No. 5, May 2003, pp. 325-332.
Mutlib, A.E. et al., "Application of Liquid Chromatography/Mass Spectrometry in Accelerating the Identification of Human Liver Cytochrome P450 Isoforms Involved in the Metabolism of Iloperidone," Journal of Pharmacology and Experimental Therapeutics, vol. 286 No. 3, Sep. 1998, pp. 1285-1293.
Subramanian, S. et al., "Receptor profile of P88-8991 and P95-12113, metabolites of the novel antipsychotic iloperidone," Progress in Neuro-Psychopharmacology & Biological Psychiatry, vol. 26 No. 3, Jan. 1, 2002, pp. 553-560.
Pickard et al., "The NPAS3 gene—emerging evidence for a role in psychiatric illness", 2006, pp. 439-448, XP-009108604, Annals of Medicine, vol. 38, No. 6, ISSN: 0785-3890.
Kelleher et al., "Advances in Atypical Antipsychotics for the Treatment of Schizophrenia: New Formulations and New Agents", pp. 249-261, XP-001079584, CNS Drugs 2002, vol. 16, No. 4, ADIS International, Auckland, NZ.
NCBI, Probe: Reagents for Functional Genomics, 2006, 1 page, XP-002503745, "Sequence-specific oligonucleotide (SSO) probe for *Homo sapiens* variation rs11851892", Probe Pr005074415.
NCBI, Probe: Reagents for Functional Genomics, Jan. 2007, 1 page, XP-002503744, "Bead microarray element (bead) probe for *Homo sapiens* variation rs11851892", Probe Pr008160271.
Sitton, Office Action Communication for U.S. Appl. No. 12/675,598 dated Aug. 7, 3024, 12 pages.
Ehrer et al., "Iloperidone: A novel atypical antipsychotic for the treatment of schizophrenia", 2008, pp. 190-196 + 203, Formulary, vol. 43, No. 6.
Sitton, Office Action Communication for U.S. Appl. No. 12/675,598 dated Dec. 31, 2012, 25 pages.

(Continued)

*Primary Examiner* — Jeanine A Goldberg
(74) *Attorney, Agent, or Firm* — Hoffman Warnick LLC

(57) ABSTRACT

Methods for predicting whether iloperidone will be efficacious in treating a psychotic symptom in an individual, based on the individual's genotype at one or more single nucleotide polymorphism (SNP) loci are described, as are methods for treating an individual based on such prediction.

13 Claims, No Drawings

(56) References Cited

OTHER PUBLICATIONS

Wei et al., "Association analysis of serotonin receptor 7 gene (HTR7) and risperidone response in Chinese schizophrenia patient," 2009, ages 547-551, Progress in Neuro-Psychopharmacology & Biological Psychiatry, vol. 33.

Lucentini, "Gene Association Studies Typically Wrong," Dec. 2004, p. 20, The Scientist, vol. 24.

Juppner, "Functional Properties of the PTH/PTHrP Receptor," 1995, pp. 39S-42S, Bone, vol. 17, No. 2.

Hegele, "SNP Judgments and Freedom of Association," 2002, pp. 1058-1061, Arteriosclerosis, Thrombosis, and Vascular Biology, Journal of the American Heart Association, vol. 22.

Sitton, Examiner Search Strategy and Results, ss24557736 (dbSNP, rs4528226; 2004) from U.S. Appl. No. 12/675,598 dated Dec. 31, 2012, 1 page.

* cited by examiner

GENETIC MARKERS FOR EFFICACY OF ILOPERIDONE IN THE TREATMENT OF PSYCHOTIC SYMPTOMS

CROSS REFERENCE TO RELATED APPLICATIONS

This application claims the benefit of U.S. Provisional Application No. 60/939,033, filed 18 May 2007, which is hereby incorporated herein.

BACKGROUND OF THE INVENTION

1. Technical Field

The invention relates generally to the treatment of psychotic symptoms, and more particularly, to predicting whether iloperidone, an iloperidone metabolite, or pharmaceutically-acceptable salts thereof will be efficacious in treating an individual's psychotic symptoms, based on the individual's genotype at one or more single nucleotide polymorphism (SNP) loci.

2. Background Art

Schizophrenia is a psychotic disorder affecting approximately 1% of the US population. It is characterized by the presence of positive symptoms (e.g., hallucinations and delusions) and negative symptoms (e.g., blunted affect and social withdrawal), as well as impairment of cognitive functions. There is much evidence that schizophrenia may not be caused by a single major gene, but rather by several interacting susceptibility loci.

The nature and severity of an individual's schizophrenia may be measured using a number of scales, the most widely used being the Positive and Negative Syndrome Scale (PANSS). A number of PANSS subscales may also be used, such as the PANSS general psychopathology subscale (PANSS-GP), the PANSS positive symptom subscale (PANSS-P), and the PANSS negative symptom subscale (PANSS-N). The PANSS total score (PANSS-T) is comprised of all PANSS subscales.

Perhaps due to the heterogeneity of the underlying disease process, the etiology of schizophrenia has not been identified. Genetic factors are expected to play a role in the response to drug treatment. Several studies have shown that a polymorphism in the serotonin 5-HT2A receptor may be associated with the efficacy of clozapine and risperidone.

Iloperidone is classified as an atypical antipsychotic, most commonly characterized by their relatively low affinity for dopamine D2 receptors and high affinity for serotonin 5-HT2 receptors. Data stemming from the iloperidone clinical program indicate that the response to iloperidone is variable, as is the case with all marketed antipsychotics.

SUMMARY OF THE INVENTION

The invention provides a method for predicting whether iloperidone is likely to be efficacious in treating psychotic symptoms, such as hallucinations and delusions, in psychiatric disorders, including schizophrenia, schizoaffective disorders, bipolar I, bipolar II, and major depression with psychiatric features, in an individual, based on the individual's genotype at one or more single nucleotide polymorphism (SNP) loci, as well as a related method for treating an individual based on such prediction.

A first aspect of the invention provides a method of predicting the efficacy of using iloperidone, an iloperidone metabolite, or a pharmaceutically-acceptable salt of iloperidone or an iloperidone metabolite in the treatment of at least one psychotic symptom in an individual, the method comprising: determining the individual's genotype at least one single nucleotide polymorphism (SNP) locus selected from a group consisting of: SNP_A-2048427, SNP_A-2283283, SNP_A-1973093, SNP_A-2284243, SNP_A-2274533, SNP_A-2076797, SNP_A-4212785, SNP_A-4230979, SNP_A-2007721, SNP_A-2170121, SNP_A-2103099, SNP_A-1975928, SNP_A-4258279, SNP_A-1934663, SNP_A-2120958, SNP_A-4204396, SNP_A-4256833, SNP_A-1860353, SNP_A-2070454, SNP_A-2044214, SNP_A-1987915, and SNP_A-1819750; and, in the case that the individual's genotype at the at least one SNP locus is associated with greater iloperidone efficacy, predicting that treating the individual with iloperidone will be efficacious.

A second aspect of the invention provides a method of treating a psychotic symptom in an individual, comprising: determining the individual's genotype at least one single nucleotide polymorphism (SNP) locus selected from a group consisting of: SNP_A-2048427, SNP_A-2283283, SNP_A-1973093, SNP_A-2284243, SNP_A-2274533, SNP_A-2076797, SNP_A-4212785, SNP_A-4230979, SNP_A-2007721, SNP_A-2170121, SNP_A-2103099, SNP_A-1975928, SNP_A-4258279, SNP_A-1934663, SNP_A-2120958, SNP_A-4204396, SNP_A-4256833, SNP_A-1860353, SNP_A-2070454, SNP_A-2044214, SNP_A-1987915, and SNP_A-1819750; and in the case that the individual's genotype at the at least one SNP locus is associated with greater iloperidone efficacy, administering to the individual a quantity of iloperidone.

A third aspect of the invention provides a method of predicting the efficacy of using iloperidone, an iloperidone metabolite, or a pharmaceutically-acceptable salt of iloperidone or an iloperidone metabolite in the treatment of at least one psychotic symptom in an individual, the method comprising: characterizing an expression product of a gene associated with at least one single nucleotide polymorphism (SNP) locus selected from a group consisting of: SNP_A-2048427, SNP_A-2283283, SNP_A-1973093, SNP_A-2284243, SNP_A-2274533, SNP_A-2076797, SNP_A-4212785, SNP_A-4230979, SNP_A-2007721, SNP_A-2170121, SNP_A-2103099, SNP_A-1975928, SNP_A-4258279, SNP_A-1934663, SNP_A-2120958, SNP_A-4204396, SNP_A-4256833, SNP_A-1860353, SNP_A-2070454, SNP_A-2044214, SNP_A-1987915, and SNP_A-1819750; and, in the case that the expression product is associated with greater iloperidone efficacy, predicting that treating the individual with iloperidone will be efficacious.

A fourth aspect of the invention provides a method of treating a psychotic symptom in an individual, comprising: characterizing an expression product of a gene associated with at least one single nucleotide polymorphism (SNP) locus selected from a group consisting of: SNP_A-2048427, SNP_A-2283283, SNP_A-1973093, SNP_A-2284243, SNP_A-2274533, SNP_A-2076797, SNP_A-4212785, SNP_A-4230979, SNP_A-2007721, SNP_A-2170121, SNP_A-2103099, SNP_A-1975928, SNP_A-4258279, SNP_A-1934663, SNP_A-2120958, SNP_A-4204396, SNP_A-4256833, SNP_A-1860353, SNP_A-2070454, SNP_A-2044214, SNP_A-1987915, and SNP_A-1819750; and, in the case that the expression product is associated with greater iloperidone efficacy, administering to the individual a quantity of iloperidone.

DETAILED DESCRIPTION

Earlier studies investigated an association between a polymorphism in the CNTF gene and iloperidone efficacy as well as associations between CYP2D6 and KCNQ1 genotypes and changes in QT interval following the administration of iloperidone. The present study involved the genotyping of DNA samples collected from 426 individuals diagnosed with schizophrenia in an attempt to identify additional SNPs associated with iloperidone efficacy.

Each sample was genotyped at more than 500,000 SNP loci using the GeneChip® Human Mapping 500K Array Set (Affymetrix, Santa Clara, Calif.) and using assays developed in-house.

Approximately half of the participants in the study were administered 24 mg/day of iloperidone, b.i.d., for 28 days. About 25% of the patients were administered ziprasidone. The remaining participants were administered a placebo.

Three analyses of the PANSS-T were conducted. 1) A two-step approach where samples were randomly split into 2 groups of iloperidone-treated patients used to discover SNPs associated with changed in PANSS-T (Discovery phase) and a second group to confirm the 100 most significant SNPs (Confirmatory phase). 2) A one-step approach using the Last Observation Carried Forward (LOCF) PANSS-T data of all iloperidone-treated patients. For each SNP, the most parsimonious genetic model (e.g., homozygous for one allele v. all other genotypes [i.e., AA v. AB and BB], heterozygous v. homozygous [i.e., AB v. AA and BB]) was established with respect to iloperidone efficacy using a one-way analysis of variance (ANOVA). 3) A Mixed-effects Model Repeated Measures (MMRM) analysis was subsequently conducted using the best genetic model of each SNP in the MMRM model. MMRM analyses were also conducted with the PANSS subscales PANSS-P, PANSS-N, and PANSS-GP.

The SNPs with a statistically significant association in all 3 analyses of PANSS-T, as well as the best of each analysis were considered significant findings and are listed below in Table 1. Results for each of these SNPs with the PANSS-T scales and with the three subscales PANSS-P, PANSS-N, and PANSS-GP are shown in Tables 2, 3, 4, and 5, respectively.

TABLE 1

SNPs associated with efficacy in iloperidone-treated patients

| SNP[1] | dbSNP[1] | Gene[2] | Chr. | Cyto | Position[3] | allele A[4] | allele B[4] | Genotype[5] |
|---|---|---|---|---|---|---|---|---|
| SNP_A-1819750 | rs2902346 | CREG1 | 1 | q24.2 | 165793447 | A | G | nonAB |
| SNP_A-1860353 | rs17105331 | RAP1B | 12 | q15 | 67030804 | A | G | AA |
| SNP_A-1934663 | rs6565249 | | 16 | p11.2 | 31476343 | A | G | nonBB |
| SNP_A-1973093 | rs875326 | KIAA0040 | 1 | q25.1 | 173556022 | A | G | nonAB |
| SNP_A-1975928 | rs16892475 | SLC2A9 | 4 | p16.1 | 9649371 | A | C | nonBB |
| SNP_A-1987915 | rs1931990 | GPR126 | 6 | q24.1 | 142638813 | A | G | BB |
| SNP_A-2007721 | rs1473470 | LOC58486 | 11 | p15.3 | 11003055 | C | G | AB |
| SNP_A-2044214 | rs7939190 | HNT | 11 | q25 | 131362795 | A | G | nonAB |
| SNP_A-2048427 | rs11851892 | NPAS3 | 14 | q13.1 | 32921165 | A | G | nonBB |
| SNP_A-2070454 | rs11744669 | NKX2-5 | 5 | q35.2 | 172657942 | A | G | BB |
| SNP_A-2076797 | rs4528226 | NUDT9P1 | 10 | q23.31 | 92822226 | G | T | AB |
| SNP_A-2103099 | rs10039523 | HTR1A | 5 | q12.1 | 62457846 | A | G | nonAB |
| SNP_A-2120958 | rs6669798 | | 1 | p33 | 48160175 | C | T | nonBB |
| SNP_A-2170121 | rs17260228 | C6 | 5 | p13.1 | 41204861 | C | T | AB |
| SNP_A-2274533 | rs7837682 | LZTS1 | 8 | p21.3 | 21329990 | A | G | AA |
| SNP_A-2283283 | rs9643483 | XKR4 | 8 | q12.1 | 55960228 | G | T | nonAA |
| SNP_A-2284243 | rs2513265 | GRIA4 | 11 | q22.3 | 104929005 | A | T | nonBB |
| SNP_A-4204396 | rs7206381 | CDH13 | 16 | q23.3 | 81620805 | C | T | nonBB |
| SNP_A-4212785 | rs17155176 | PPP1R3B | 8 | p23.1 | 8973511 | C | T | nonAA |
| SNP_A-4230979 | rs13019052 | ASB3 | 2 | p16.2 | 52901041 | C | G | BB |
| SNP_A-4256833 | rs4401068 | MLCK | 16 | q11.2 | 45354669 | A | G | nonAB |
| SNP_A-4258279 | rs7946885 | RRM1 | 11 | p15.4 | 4120756 | A | G | nonAB |

[1]SNPs are identified by their Affymetrix SNP nomenclature (SNP_A-) and their unique dbSNP number (http://www.ncbi.nlm.nih.gov/projects/SNP/) dbSNP version 126, May 2006.
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]The address of each SNP in the genome is indicated by its chromosome (Chr.), cytoband (Cyto), location and the physical position as listed in the NCBI Build 36.1, March 2006 (http://www.ncbi.nlm.nih.gov/entrez/query.fcgi?db=snp)
[4]The nucleotides corresponding to the A and B alleles are listed as defined by Affymetrix. Their relation of the + and − strands is available at the NCBI dbSNP web site listed above.
[5]The genotype class associated with better iloperidone response is shown using the Affymetrix allele nomenclature.

TABLE 2

SNPs associated with PANSS-T score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-1934663 | | 5.42404E−05 | 0.072815255 | A_A | 15 | −18.67 | 3.20 |
| | | 5.42404E−05 | 0.072815255 | A_B | 58 | −18.34 | 4.25 |
| | | 5.42404E−05 | 0.072815255 | B_B* | 115 | −8.39 | 4.71 |
| | | 5.42404E−05 | 0.072815255 | nonBB** | 73 | −18.40 | 4.04 |
| SNP_A-1973093 | KIAA0040 | 2.11212E−05 | 0.000607322 | A_A | 25 | −14.99 | 4.27 |
| | | 2.11212E−05 | 0.000607322 | A_B* | 76 | −6.21 | 4.51 |
| | | 2.11212E−05 | 0.000607322 | B_B | 105 | −16.73 | 4.33 |
| | | 2.11212E−05 | 0.000607322 | nonAB** | 130 | −16.39 | 4.35 |
| SNP_A-2070454 | NKX2-5 | 0.000646006 | 0.000122264 | A_A | 44 | −9.88 | 5.04 |
| | | 0.000646006 | 0.000122264 | A_B | 94 | −10.39 | 4.07 |
| | | 0.000646006 | 0.000122264 | B_B** | 61 | −18.31 | 4.43 |
| | | 0.000646006 | 0.000122264 | nonBB* | 138 | −10.23 | 4.39 |

TABLE 2-continued

SNPs associated with PANSS-T score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-2076797 | NUDT9P1 | 7.78445E−07 | 0.015918222 | A_A | 57 | −7.14 | 4.10 |
| | | 7.78445E−07 | 0.015918222 | A_B** | 99 | −18.73 | 3.99 |
| | | 7.78445E−07 | 0.015918222 | B_B | 52 | −6.04 | 4.45 |
| | | 7.78445E−07 | 0.015918222 | nonAB* | 109 | −6.61 | 4.29 |
| SNP_A-2103099 | HTR1A | 3.13417E−05 | 5.86485E−07 | A_A | 38 | −17.43 | 4.64 |
| | | 3.13417E−05 | 5.86485E−07 | A_B* | 105 | −8.31 | 4.34 |
| | | 3.13417E−05 | 5.86485E−07 | B_B | 65 | −16.12 | 4.21 |
| | | 3.13417E−05 | 5.86485E−07 | nonAB** | 103 | −16.60 | 4.40 |
| SNP_A-2120958 | | 7.60281E−05 | 0.00188507 | A_A | 116 | −13.95 | 4.28 |
| | | 7.60281E−05 | 0.00188507 | A_B | 77 | −13.71 | 4.67 |
| | | 7.60281E−05 | 0.00188507 | B_B* | 17 | 2.48 | 5.38 |
| | | 7.60281E−05 | 0.00188507 | nonBB** | 193 | −13.85 | 4.43 |
| SNP_A-2170121 | C6 | 1.69136E−05 | 0.000229991 | A_A | 137 | −8.94 | 4.27 |
| | | 1.69136E−05 | 0.000229991 | A_B** | 53 | −21.93 | 3.86 |
| | | 1.69136E−05 | 0.000229991 | B_B | 14 | −11.50 | 3.58 |
| | | 1.69136E−05 | 0.000229991 | nonAB* | 151 | −9.17 | 4.27 |
| SNP_A-2283283 | XKR4 | 0.000172366 | 0.000425434 | A_A* | 47 | −3.30 | 3.93 |
| | | 0.000172366 | 0.000425434 | A_B | 96 | −14.57 | 4.35 |
| | | 0.000172366 | 0.000425434 | B_B | 67 | −15.66 | 4.28 |
| | | 0.000172366 | 0.000425434 | nonAA** | 163 | −15.02 | 4.34 |
| SNP_A-4256833 | MLCK | 0.000353368 | 0.002609391 | A_A | 9 | −15.19 | 3.02 |
| | | 0.000353368 | 0.002609391 | A_B* | 64 | −6.20 | 5.21 |
| | | 0.000353368 | 0.002609391 | B_B | 137 | −15.15 | 4.23 |
| | | 0.000353368 | 0.002609391 | nonAB** | 146 | −15.15 | 4.15 |
| SNP_A-4258279 | RRM1 | 4.67654E−05 | 0.005619516 | A_A | 2 | −13.42 | 3.08 |
| | | 4.67654E−05 | 0.005619516 | A_B* | 45 | −2.55 | 4.42 |
| | | 4.67654E−05 | 0.005619516 | B_B | 160 | −14.72 | 4.15 |
| | | 4.67654E−05 | 0.005619516 | nonAB** | 162 | −14.70 | 4.13 |
| SNP_A-1819750 | CREG1 | 0.017284377 | 0.100418357 | A_A* | 22 | −18.13 | 4.58 |
| | | 0.017284377 | 0.100418357 | A_B* | 119 | −10.74 | 4.70 |
| | | 0.017284377 | 0.100418357 | B_B | 46 | −16.05 | 4.74 |
| | | 0.017284377 | 0.100418357 | nonAB** | 68 | −16.72 | 4.76 |
| SNP_A-1860353 | RAP1B | 0.000625325 | 0.005405007 | A_A** | 5 | −37.40 | 4.03 |
| | | 0.000625325 | 0.005405007 | A_B | 35 | −11.79 | 4.23 |
| | | 0.000625325 | 0.005405007 | B_B | 169 | −11.84 | 4.03 |
| | | 0.000625325 | 0.005405007 | nonAA* | 204 | −11.83 | 4.06 |
| SNP_A-1975928 | SLC2A9 | 4.61282E−05 | 0.003653312 | A_A | 150 | −13.09 | 4.57 |
| | | 4.61282E−05 | 0.003653312 | A_B | 48 | −13.17 | 4.05 |
| | | 4.61282E−05 | 0.003653312 | B_B* | 6 | 16.38 | 6.49 |
| | | 4.61282E−05 | 0.003653312 | nonBB** | 198 | −13.11 | 4.44 |
| SNP_A-1987915 | GPR126 | 0.001249144 | 0.029776522 | A_A | 27 | −9.87 | 5.11 |
| | | 0.001249144 | 0.029776522 | A_B | 97 | −9.61 | 4.60 |
| | | 0.001249144 | 0.029776522 | B_B** | 85 | −17.29 | 4.25 |
| | | 0.001249144 | 0.029776522 | nonBB* | 124 | −9.67 | 4.69 |
| SNP_A-2007721 | LOC58486 | 1.0792E−05 | 0.000560557 | A_A | 1 | −4.55 | |
| | | 1.0792E−05 | 0.000560557 | A_B** | 48 | −22.64 | 4.50 |
| | | 1.0792E−05 | 0.000560557 | B_B | 147 | −9.55 | 3.93 |
| | | 1.0792E−05 | 0.000560557 | nonAB* | 148 | −9.52 | 3.94 |
| SNP_A-2044214 | HNT | 0.000944901 | 0.002995624 | A_A | 86 | −15.71 | 4.97 |
| | | 0.000944901 | 0.002995624 | A_B* | 78 | −7.43 | 3.87 |
| | | 0.000944901 | 0.002995624 | B_B | 46 | −14.43 | 4.27 |
| | | 0.000944901 | 0.002995624 | nonAB** | 132 | −15.26 | 4.76 |
| SNP_A-2048427 | NPAS3 | 9.30226E−05 | 0.008990872 | A_A | 9 | −19.94 | 2.44 |
| | | 9.30226E−05 | 0.008990872 | A_B | 56 | −20.15 | 3.87 |
| | | 9.30226E−05 | 0.008990872 | B_B* | 145 | −9.20 | 4.25 |
| | | 9.30226E−05 | 0.008990872 | nonBB** | 65 | −20.12 | 3.69 |
| SNP_A-2274533 | LZTS1 | 0.000180835 | 0.00115156 | A_A** | 116 | −15.95 | 4.23 |
| | | 0.000180835 | 0.00115156 | A_B | 64 | −6.04 | 4.55 |
| | | 0.000180835 | 0.00115156 | B_B | 18 | −6.21 | 3.21 |
| | | 0.000180835 | 0.00115156 | nonAA* | 82 | −6.08 | 4.28 |
| SNP_A-2284243 | GRIA4 | 5.54999E−05 | 0.001000122 | A_A | 63 | −15.30 | 4.46 |
| | | 5.54999E−05 | 0.001000122 | A_B | 99 | −15.17 | 4.16 |
| | | 5.54999E−05 | 0.001000122 | B_B* | 48 | −3.30 | 4.11 |
| | | 5.54999E−05 | 0.001000122 | nonBB** | 162 | −15.22 | 4.26 |
| SNP_A-4204396 | CDH13 | 8.05822E−05 | 0.005999381 | A_A | 111 | −13.72 | 4.52 |
| | | 8.05822E−05 | 0.005999381 | A_B | 67 | −14.04 | 4.02 |
| | | 8.05822E−05 | 0.005999381 | B_B* | 15 | 4.89 | 5.46 |
| | | 8.05822E−05 | 0.005999381 | nonBB** | 178 | −13.84 | 4.33 |
| SNP_A-4212785 | PPP1R3B | 2.46186E−06 | 0.002306863 | A_A* | 4 | 25.90 | 3.38 |
| | | 2.46186E−06 | 0.002306863 | A_B | 67 | −13.66 | 4.31 |
| | | 2.46186E−06 | 0.002306863 | B_B | 124 | −13.56 | 4.19 |
| | | 2.46186E−06 | 0.002306863 | nonAA** | 191 | −13.60 | 4.22 |

TABLE 2-continued

SNPs associated with PANSS-T score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-4230979 | ASB3 | 6.05937E−06 | 9.86017E−05 | A_A | 26 | −6.70 | 3.39 |
| | | 6.05937E−06 | 9.86017E−05 | A_B | 98 | −8.77 | 4.59 |
| | | 6.05937E−06 | 9.86017E−05 | B_B** | 85 | −18.82 | 4.25 |
| | | 6.05937E−06 | 9.86017E−05 | nonBB* | 124 | −8.34 | 4.43 |

[1]SNPs are identified by their Affymetrix SNP nomenclature (SNP_A-)
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]p value of the MMRM analysis between the 2 genotype classes associated with lowest * or highest ** response to iloperidone treatment
[4]p value of the MMRM analysis between the iloperidone (Ilo) and placebo (Pbo) groups for the genotype class associated with the better response (**).
[5]The 2 genotypes classes used in the MMRM analyses are indicated as associated with lowest * or highest ** response to iloperidone treatment.
[6]The number of patients (N), the mean of change in PANSS-T (Mean), and the standard deviation of the mean (Std) shown here are derived from the MMRM analysis done within the group of iloperidone-treated patients.

As used herein, "greater iloperidone efficacy" means an improvement in PANSS-T score of at least about 20%. In the current study, this means an improvement of at least 13 points.

The predictive potential of a SNP may be better appreciated when expressed in terms of an Odds Ratio (likelihood that an individual having a genotype associated with greater iloperidone efficacy will experience greater iloperidone efficacy than would an individual not having a genotype associated with greater iloperidone efficacy), Sensitivity (probability that an individual with have a genotype associated with greater iloperidone efficacy, given that he/she experience greater iloperidone efficacy), Specificity (probability that an individual will not have a genotype associated with greater iloperidone efficacy, given that he/she does not experience greater iloperidone efficacy), negative predictive value (probability that an individual will not experience greater iloperidone efficacy, given that he/she does not have a genotype associated with greater iloperidone efficacy), and positive predictive value (probability that an individual will experience greater iloperidone efficacy, given that he/she has a genotype associated with greater iloperidone efficacy). These values are shown in Table 6 below.

Among the 6 SNPs identified in all 3 analyses of PANSS-T and listed in Table 6, SNP_A-2048427 was the SNP with the highest specificity (79%) and best positive predictive value (62%). The SNPs with the highest sensitivity (87%) were SNP_A-2274533 and SNP_A-2283283. These SNPs also provided the best negative predictive values (75% and 74%, respectively).

Interestingly, the effect of these SNPs on each of the PANSS subscales varied. For example, SNP_A-2076797 exhibited the strongest association in the PANSS-P subscale, SNP_A-2274533 exhibited the strongest association in the PANSS-N subscale, and SNP_A-1973093 exhibited the strongest association in the PANSS-GP subscale. These results are shown below in Tables 3-5 and underscore the value of evaluating several genetic markers when analyzing a clinical phenotype as complex as drug response. In the present case of iloperidone efficacy, it is likely that different markers are more specifically associated with one or a few specific clinical symptoms, which is reflected in the improvement measured in separate subscales.

TABLE 3

SNPs associated with PANSS-P score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-1934663 | | 0.003905021 | 0.017701441 | A_A | 15 | −5.65 | 1.43 |
| | | 0.003905021 | 0.017701441 | A_B | 58 | −5.78 | 1.49 |
| | | 0.003905021 | 0.017701441 | B_B* | 115 | −3.40 | 1.71 |
| | | 0.003905021 | 0.017701441 | nonBB** | 73 | −5.75 | 1.47 |
| SNP_A-1973093 | KIAA0040 | 0.00037196 | 0.000125358 | A_A | 25 | −5.12 | 1.46 |
| | | 0.00037196 | 0.000125358 | A_B* | 76 | −2.58 | 1.54 |
| | | 0.00037196 | 0.000125358 | B_B | 105 | −5.64 | 1.47 |
| | | 0.00037196 | 0.000125358 | nonAB** | 130 | −5.54 | 1.47 |
| SNP_A-2070454 | NKX2-5 | 0.024690788 | 0.000399844 | A_A | 44 | −4.04 | 1.83 |
| | | 0.024690788 | 0.000399844 | A_B | 94 | −3.89 | 1.38 |
| | | 0.024690788 | 0.000399844 | B_B** | 61 | −5.75 | 1.46 |
| | | 0.024690788 | 0.000399844 | nonBB* | 138 | −3.94 | 1.54 |
| SNP_A-2076797 | NUDT9P1 | 1.67719E−07 | 5.22823E−05 | A_A | 57 | −2.57 | 1.37 |
| | | 1.67719E−07 | 5.22823E−05 | A_B** | 99 | −6.55 | 1.39 |
| | | 1.67719E−07 | 5.22823E−05 | B_B | 52 | −2.27 | 1.53 |
| | | 1.67719E−07 | 5.22823E−05 | nonAB* | 109 | −2.42 | 1.45 |
| SNP_A-2103099 | HTR1A | 4.37186E−06 | 2.53636E−08 | A_A | 38 | −6.05 | 1.72 |
| | | 4.37186E−06 | 2.53636E−08 | A_B* | 105 | −2.88 | 1.41 |
| | | 4.37186E−06 | 2.53636E−08 | B_B | 65 | −5.88 | 1.47 |
| | | 4.37186E−06 | 2.53636E−08 | nonAB** | 103 | −5.95 | 1.56 |
| SNP_A-2120958 | | 4.54898E−06 | 1.76898E−05 | A_A | 116 | −4.97 | 1.48 |
| | | 4.54898E−06 | 1.76898E−05 | A_B | 77 | −4.92 | 1.48 |
| | | 4.54898E−06 | 1.76898E−05 | B_B* | 17 | 1.49 | 1.47 |
| | | 4.54898E−06 | 1.76898E−05 | nonBB** | 193 | −4.95 | 1.48 |

TABLE 3-continued

SNPs associated with PANSS-P score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-2170121 | C6 | 0.00039812 | 2.77139E-05 | A_A | 137 | -3.49 | 1.47 |
| | | 0.00039812 | 2.77139E-05 | A_B** | 53 | -6.98 | 1.35 |
| | | 0.00039812 | 2.77139E-05 | B_B | 14 | -4.26 | 1.00 |
| | | 0.00039812 | 2.77139E-05 | nonAB* | 151 | -3.56 | 1.45 |
| SNP_A-2283283 | XKR4 | 0.001976376 | 8.73988E-06 | A_A* | 47 | -1.85 | 1.41 |
| | | 0.001976376 | 8.73988E-06 | A_B | 96 | -4.92 | 1.34 |
| | | 0.001976376 | 8.73988E-06 | B_B | 67 | -5.41 | 1.48 |
| | | 0.001976376 | 8.73988E-06 | nonAA** | 163 | -5.12 | 1.42 |
| SNP_A-4256833 | MLCK | 0.002452989 | 0.000199725 | A_A | 9 | -4.59 | 1.17 |
| | | 0.002452989 | 0.000199725 | A_B* | 64 | -2.78 | 1.82 |
| | | 0.002452989 | 0.000199725 | B_B | 137 | -5.14 | 1.37 |
| | | 0.002452989 | 0.000199725 | nonAB** | 146 | -5.10 | 1.36 |
| SNP_A-4258279 | RRM1 | 5.11554E-06 | 5.0386E-05 | A_A | 2 | -5.01 | 0.99 |
| | | 5.11554E-06 | 5.0386E-05 | A_B* | 45 | -0.85 | 1.64 |
| | | 5.11554E-06 | 5.0386E-05 | B_B | 160 | -5.25 | 1.43 |
| | | 5.11554E-06 | 5.0386E-05 | nonAB** | 162 | -5.24 | 1.43 |
| SNP_A-1819750 | CREG1 | 0.274067436 | 0.042539637 | A_A | 22 | -5.31 | 1.37 |
| | | 0.274067436 | 0.042539637 | A_B* | 119 | -4.28 | 1.48 |
| | | 0.274067436 | 0.042539637 | B_B | 46 | -5.02 | 1.51 |
| | | 0.274067436 | 0.042539637 | nonAB** | 68 | -5.11 | 1.46 |
| SNP_A-1860353 | RAP1B | 0.041832082 | 0.04007533 | A_A** | 5 | -9.20 | 1.41 |
| | | 0.041832082 | 0.04007533 | A_B | 35 | -4.42 | 1.59 |
| | | 0.041832082 | 0.04007533 | B_B | 169 | -4.28 | 1.37 |
| | | 0.041832082 | 0.04007533 | nonAA* | 204 | -4.30 | 1.40 |
| SNP_A-1975928 | SLC2A9 | 1.50144E-06 | 9.32666E-05 | A_A | 150 | -4.60 | 1.62 |
| | | 1.50144E-06 | 9.32666E-05 | A_B | 48 | -4.79 | 1.49 |
| | | 1.50144E-06 | 9.32666E-05 | B_B* | 6 | 6.19 | 2.08 |
| | | 1.50144E-06 | 9.32666E-05 | nonBB** | 198 | -4.65 | 1.59 |
| SNP_A-1987915 | GPR126 | 0.001751883 | 0.002962652 | A_A | 27 | -3.53 | 1.49 |
| | | 0.001751883 | 0.002962652 | A_B | 97 | -3.43 | 1.53 |
| | | 0.001751883 | 0.002962652 | B_B** | 85 | -5.95 | 1.35 |
| | | 0.001751883 | 0.002962652 | nonBB* | 124 | -3.45 | 1.52 |
| SNP_A-2007721 | LOC58486 | 5.7801E-05 | 0.000580283 | A_A | 1 | -1.70 | |
| | | 5.7801E-05 | 0.000580283 | A_B** | 48 | -7.48 | 1.51 |
| | | 5.7801E-05 | 0.000580283 | B_B | 147 | -3.42 | 1.35 |
| | | 5.7801E-05 | 0.000580283 | nonAB* | 148 | -3.41 | 1.35 |
| SNP_A-2044214 | HNT | 2.5043E-06 | 8.84357E-06 | A_A | 86 | -5.77 | 1.53 |
| | | 2.5043E-06 | 8.84357E-06 | A_B* | 78 | -2.08 | 1.36 |
| | | 2.5043E-06 | 8.84357E-06 | B_B | 46 | -5.64 | 1.37 |
| | | 2.5043E-06 | 8.84357E-06 | nonAB** | 132 | -5.73 | 1.47 |
| SNP_A-2048427 | NPAS3 | 0.004724236 | 0.002047518 | A_A | 9 | -6.16 | 0.74 |
| | | 0.004724236 | 0.002047518 | A_B | 56 | -6.26 | 1.35 |
| | | 0.004724236 | 0.002047518 | B_B* | 145 | -3.61 | 1.46 |
| | | 0.004724236 | 0.002047518 | nonBB** | 65 | -6.24 | 1.28 |
| SNP_A-2274533 | LZTS1 | 0.002564762 | 0.000131854 | A_A** | 116 | -5.34 | 1.47 |
| | | 0.002564762 | 0.000131854 | A_B | 64 | -2.64 | 1.57 |
| | | 0.002564762 | 0.000131854 | B_B | 18 | -2.63 | 0.95 |
| | | 0.002564762 | 0.000131854 | nonAA* | 82 | -2.63 | 1.45 |
| SNP_A-2284243 | GRIA4 | 0.002257083 | 0.000446623 | A_A | 63 | -5.09 | 1.49 |
| | | 0.002257083 | 0.000446623 | A_B | 99 | -5.09 | 1.51 |
| | | 0.002257083 | 0.000446623 | B_B* | 48 | -2.11 | 1.28 |
| | | 0.002257083 | 0.000446623 | nonBB** | 162 | -5.09 | 1.49 |
| SNP_A-4204396 | CDH13 | 8.30622E-06 | 0.000224593 | A_A | 111 | -4.76 | 1.60 |
| | | 8.30622E-06 | 0.000224593 | A_B | 67 | -4.99 | 1.31 |
| | | 8.30622E-06 | 0.000224593 | B_B* | 15 | 1.63 | 1.90 |
| | | 8.30622E-06 | 0.000224593 | nonBB** | 178 | -4.85 | 1.50 |
| SNP_A-4212785 | PPP1R3B | 0.000861132 | 1.17771E-05 | A_A* | 4 | 4.95 | 1.17 |
| | | 0.000861132 | 1.17771E-05 | A_B | 67 | -4.78 | 1.34 |
| | | 0.000861132 | 1.17771E-05 | B_B | 124 | -4.70 | 1.46 |
| | | 0.000861132 | 1.17771E-05 | nonAA** | 191 | -4.73 | 1.42 |
| SNP_A-4230979 | ASB3 | 0.001139814 | 0.000253507 | A_A | 26 | -2.80 | 1.12 |
| | | 0.001139814 | 0.000253507 | A_B | 98 | -3.63 | 1.52 |
| | | 0.001139814 | 0.000253507 | B_B** | 85 | -5.84 | 1.51 |
| | | 0.001139814 | 0.000253507 | nonBB* | 124 | -3.45 | 1.48 |

[1]SNPs are identified by their Affymetrix SNP nomenclature (SNP_A-)
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]p value of the MMRM analysis between the 2 genotype classes associated with lowest * or highest ** response to iloperidone treatment
[4]p value of the MMRM analysis between the iloperidone (Ilo) and placebo (Pbo) groups for the genotype class associated with the better response (**).
[5]The 2 genotypes classes used in the MMRM analyses are indicated as associated with lowest * or highest ** response to iloperidone treatment.
[6]The number of patients (N), the mean of change in PANSS-P (Mean), and the standard deviation of the mean (Std) shown here are derived from the MMRM analysis done within the group of iloperidone-treated patients.

TABLE 4

SNPs associated with PANSS-N score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-1934663 |  | 0.002008934 | 0.418799746 | A_A | 15 | −3.38 | 1.84 |
|  |  | 0.002008934 | 0.418799746 | A_B | 58 | −3.94 | 2.10 |
|  |  | 0.002008934 | 0.418799746 | B_B* | 115 | −2.06 | 1.97 |
|  |  | 0.002008934 | 0.418799746 | nonBB** | 73 | −3.82 | 2.05 |
| SNP_A-1973093 | KIAA0040 | 0.007114056 | 0.068955252 | A_A | 25 | −3.32 | 1.91 |
|  |  | 0.007114056 | 0.068955252 | A_B* | 76 | −1.85 | 1.96 |
|  |  | 0.007114056 | 0.068955252 | B_B | 105 | −3.46 | 1.96 |
|  |  | 0.007114056 | 0.068955252 | nonAB** | 130 | −3.43 | 1.94 |
| SNP_A-2070454 | NKX2-5 | 4.97557E−05 | 8.03515E−05 | A_A | 44 | −1.86 | 2.21 |
|  |  | 4.97557E−05 | 8.03515E−05 | A_B | 94 | −2.40 | 1.98 |
|  |  | 4.97557E−05 | 8.03515E−05 | B_B** | 61 | −4.58 | 2.02 |
|  |  | 4.97557E−05 | 8.03515E−05 | nonBB* | 138 | −2.23 | 2.06 |
| SNP_A-2076797 | NUDT9P1 | 0.000463402 | 0.080014935 | A_A | 57 | −1.75 | 2.10 |
|  |  | 0.000463402 | 0.080014935 | A_B** | 99 | −4.06 | 1.89 |
|  |  | 0.000463402 | 0.080014935 | B_B | 52 | −1.62 | 1.78 |
|  |  | 0.000463402 | 0.080014935 | nonAB* | 109 | −1.69 | 1.94 |
| SNP_A-2103099 | HTR1A | 0.000979899 | 0.000198436 | A_A | 38 | −4.08 | 1.97 |
|  |  | 0.000979899 | 0.000198436 | A_B* | 105 | −2.09 | 1.99 |
|  |  | 0.000979899 | 0.000198436 | B_B | 65 | −3.40 | 1.85 |
|  |  | 0.000979899 | 0.000198436 | nonAB** | 103 | −3.65 | 1.91 |
| SNP_A-2120958 |  | 0.017774444 | 0.071168568 | A_A | 116 | −3.15 | 1.88 |
|  |  | 0.017774444 | 0.071168568 | A_B | 77 | −2.84 | 2.06 |
|  |  | 0.017774444 | 0.071168568 | B_B* | 17 | −1.11 | 2.13 |
|  |  | 0.017774444 | 0.071168568 | nonBB** | 193 | −3.03 | 1.96 |
| SNP_A-2170121 | C6 | 0.001634307 | 0.016887418 | A_A | 137 | −2.14 | 1.85 |
|  |  | 0.001634307 | 0.016887418 | A_B** | 53 | −4.78 | 2.22 |
|  |  | 0.001634307 | 0.016887418 | B_B | 14 | −2.52 | 1.78 |
|  |  | 0.001634307 | 0.016887418 | nonAB* | 151 | −2.17 | 1.84 |
| SNP_A-2283283 | XKR4 | 0.002331952 | 0.018382642 | A_A* | 47 | −0.95 | 1.47 |
|  |  | 0.002331952 | 0.018382642 | A_B | 96 | −3.20 | 2.06 |
|  |  | 0.002331952 | 0.018382642 | B_B | 67 | −3.62 | 1.99 |
|  |  | 0.002331952 | 0.018382642 | nonAA** | 163 | −3.37 | 2.03 |
| SNP_A-4256833 | MLCK | 4.46659E−05 | 0.02283654 | A_A | 9 | −3.58 | 1.63 |
|  |  | 4.46659E−05 | 0.02283654 | A_B* | 64 | −0.86 | 2.04 |
|  |  | 4.46659E−05 | 0.02283654 | B_B | 137 | −3.69 | 1.90 |
|  |  | 4.46659E−05 | 0.02283654 | nonAB** | 146 | −3.68 | 1.88 |
| SNP_A-4258279 | RRM1 | 0.012725795 | 0.202301911 | A_A | 2 | −2.57 | 0.37 |
|  |  | 0.012725795 | 0.202301911 | A_B* | 45 | −1.09 | 1.96 |
|  |  | 0.012725795 | 0.202301911 | B_B | 160 | −3.34 | 1.85 |
|  |  | 0.012725795 | 0.202301911 | nonAB** | 162 | −3.33 | 1.84 |
| SNP_A-1819750 | CREG1 | 6.64422E−05 | 0.03950581 | A_A | 22 | −5.35 | 1.71 |
|  |  | 6.64422E−05 | 0.03950581 | A_B* | 119 | −2.01 | 2.12 |
|  |  | 6.64422E−05 | 0.03950581 | B_B | 46 | −4.01 | 1.93 |
|  |  | 6.64422E−05 | 0.03950581 | nonAB** | 68 | −4.45 | 1.95 |
| SNP_A-1860353 | RAP1B | 1.56517E−05 | 0.001522569 | A_A** | 5 | −11.00 | 2.13 |
|  |  | 1.56517E−05 | 0.001522569 | A_B | 35 | −2.29 | 2.04 |
|  |  | 1.56517E−05 | 0.001522569 | B_B | 169 | −2.73 | 1.82 |
|  |  | 1.56517E−05 | 0.001522569 | nonAA* | 204 | −2.65 | 1.86 |
| SNP_A-1975928 | SLC2A9 | 0.017253052 | 0.094589657 | A_A | 150 | −2.87 | 1.94 |
|  |  | 0.017253052 | 0.094589657 | A_B | 48 | −2.95 | 1.57 |
|  |  | 0.017253052 | 0.094589657 | B_B* | 6 | 0.62 | 2.79 |
|  |  | 0.017253052 | 0.094589657 | nonBB** | 198 | −2.89 | 1.86 |
| SNP_A-1987915 | GPR126 | 3.12808E−05 | 0.022414357 | A_A | 27 | −1.91 | 2.49 |
|  |  | 3.12808E−05 | 0.022414357 | A_B | 97 | −2.03 | 2.00 |
|  |  | 3.12808E−05 | 0.022414357 | B_B** | 85 | −4.28 | 1.93 |
|  |  | 3.12808E−05 | 0.022414357 | nonBB* | 124 | −2.00 | 2.11 |
| SNP_A-2007721 | LOC58486 | 0.000980061 | 0.00971944 | A_A | 1 | 0.51 |  |
|  |  | 0.000980061 | 0.00971944 | A_B** | 48 | −4.73 | 1.93 |
|  |  | 0.000980061 | 0.00971944 | B_B | 147 | −2.33 | 1.95 |
|  |  | 0.000980061 | 0.00971944 | nonAB* | 148 | −2.31 | 1.95 |
| SNP_A-2044214 | HNT | 0.040382222 | 0.031333432 | A_A | 86 | −3.32 | 2.11 |
|  |  | 0.040382222 | 0.031333432 | A_B* | 78 | −2.16 | 1.94 |
|  |  | 0.040382222 | 0.031333432 | B_B | 46 | −3.05 | 1.76 |
|  |  | 0.040382222 | 0.031333432 | nonAB** | 132 | −3.22 | 1.99 |
| SNP_A-2048427 | NPAS3 | 0.002823078 | 0.039237616 | A_A | 9 | −4.12 | 1.41 |
|  |  | 0.002823078 | 0.039237616 | A_B | 56 | −4.30 | 1.97 |
|  |  | 0.002823078 | 0.039237616 | B_B* | 145 | −2.27 | 1.96 |
|  |  | 0.002823078 | 0.039237616 | nonBB** | 65 | −4.28 | 1.89 |
| SNP_A-2274533 | LZTS1 | 0.000653736 | 0.01900311 | A_A** | 116 | −3.67 | 2.03 |
|  |  | 0.000653736 | 0.01900311 | A_B | 64 | −1.52 | 1.84 |
|  |  | 0.000653736 | 0.01900311 | B_B | 18 | −1.16 | 2.05 |
|  |  | 0.000653736 | 0.01900311 | nonAA* | 82 | −1.44 | 1.88 |
| SNP_A-2284243 | GRIA4 | 7.94158E−05 | 0.010014455 | A_A | 63 | −3.70 | 1.86 |
|  |  | 7.94158E−05 | 0.010014455 | A_B | 99 | −3.46 | 1.95 |
|  |  | 7.94158E−05 | 0.010014455 | B_B* | 48 | −0.52 | 1.95 |
|  |  | 7.94158E−05 | 0.010014455 | nonBB** | 162 | −3.55 | 1.91 |

TABLE 4-continued

SNPs associated with PANSS-N score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-4204396 | CDH13 | 0.001334144 | 0.051404328 | A_A | 111 | −3.22 | 1.90 |
|  |  | 0.001334144 | 0.051404328 | A_B | 67 | −3.12 | 1.93 |
|  |  | 0.001334144 | 0.051404328 | B_B* | 15 | 1.62 | 2.13 |
|  |  | 0.001334144 | 0.051404328 | nonBB** | 178 | −3.18 | 1.91 |
| SNP_A-4212785 | PPP1R3B | 5.46916E−05 | 0.047157777 | A_A* | 4 | 4.72 | 1.29 |
|  |  | 5.46916E−05 | 0.047157777 | A_B | 67 | −3.06 | 2.09 |
|  |  | 5.46916E−05 | 0.047157777 | B_B | 124 | −3.11 | 1.82 |
|  |  | 5.46916E−05 | 0.047157777 | nonAA** | 191 | −3.09 | 1.92 |
| SNP_A-4230979 | ASB3 | 4.20913E−05 | 0.004329523 | A_A | 26 | −1.72 | 1.61 |
|  |  | 4.20913E−05 | 0.004329523 | A_B | 98 | −2.02 | 1.96 |
|  |  | 4.20913E−05 | 0.004329523 | B_B** | 85 | −4.23 | 2.01 |
|  |  | 4.20913E−05 | 0.004329523 | nonBB* | 124 | −1.96 | 1.89 |

[1]SNPs are identified by their Affymetrix SNP nomenclature (SNP_A-)
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]p value of the MMRM analysis between the 2 genotype classes associated with lowest * or highest ** response to iloperidone treatment
[4]p value of the MMRM analysis between the iloperidone (Ilo) and placebo (Pbo) groups for the genotype class associated with the better response (**).
[5]The 2 genotypes classes used in the MMRM analyses are indicated as associated with lowest * or highest ** response to iloperidone treatment.
[6]The number of patients (N), the mean of change in PANSS-N (Mean), and the standard deviation of the mean (Std) shown here are derived from the MMRM analysis done within the group of iloperidone-treated patients.

TABLE 5

SNPs associated with PANSS-GP score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-1934663 |  | 6.70172E−06 | 0.133256964 | A_A | 15 | −9.38 | 2.88 |
|  |  | 6.70172E−06 | 0.133256964 | A_B | 58 | −8.80 | 2.62 |
|  |  | 6.70172E−06 | 0.133256964 | B_B* | 115 | −3.07 | 3.33 |
|  |  | 6.70172E−06 | 0.133256964 | nonBB** | 73 | −8.92 | 2.67 |
| SNP_A-1973093 | KIAA0040 | 5.76184E−06 | 0.001577176 | A_A | 25 | −6.40 | 2.49 |
|  |  | 5.76184E−06 | 0.001577176 | A_B* | 76 | −1.92 | 2.97 |
|  |  | 5.76184E−06 | 0.001577176 | B_B | 105 | −7.77 | 3.19 |
|  |  | 5.76184E−06 | 0.001577176 | nonAB** | 130 | −7.51 | 3.11 |
| SNP_A-2070454 | NKX2-5 | 0.001508458 | 0.00202546 | A_A | 44 | −3.91 | 3.30 |
|  |  | 0.001508458 | 0.00202546 | A_B | 94 | −4.34 | 3.01 |
|  |  | 0.001508458 | 0.00202546 | B_B** | 61 | −8.12 | 2.94 |
|  |  | 0.001508458 | 0.00202546 | nonBB* | 138 | −4.20 | 3.10 |
| SNP_A-2076797 | NUDT9P1 | 3.36249E−05 | 0.17099973 | A_A | 57 | −2.80 | 2.91 |
|  |  | 3.36249E−05 | 0.17099973 | A_B** | 99 | −8.23 | 2.98 |
|  |  | 3.36249E−05 | 0.17099973 | B_B | 52 | −2.42 | 2.96 |
|  |  | 3.36249E−05 | 0.17099973 | nonAB* | 109 | −2.62 | 2.93 |
| SNP_A-2103099 | HTR1A | 0.000311502 | 4.11695E−05 | A_A | 38 | −7.79 | 3.22 |
|  |  | 0.000311502 | 4.11695E−05 | A_B* | 105 | −3.42 | 3.15 |
|  |  | 0.000311502 | 4.11695E−05 | B_B | 65 | −6.80 | 2.76 |
|  |  | 0.000311502 | 4.11695E−05 | nonAB** | 103 | −7.16 | 2.96 |
| SNP_A-2120958 |  | 0.000314352 | 0.020369025 | A_A | 116 | −5.90 | 3.01 |
|  |  | 0.000314352 | 0.020369025 | A_B | 77 | −6.13 | 3.24 |
|  |  | 0.000314352 | 0.020369025 | B_B* | 17 | 1.80 | 3.79 |
|  |  | 0.000314352 | 0.020369025 | nonBB** | 193 | −5.99 | 3.10 |
| SNP_A-2170121 | C6 | 3.69457E−05 | 0.002035176 | A_A | 137 | −3.40 | 2.88 |
|  |  | 3.69457E−05 | 0.002035176 | A_B** | 53 | −10.21 | 2.69 |
|  |  | 3.69457E−05 | 0.002035176 | B_B | 14 | −5.25 | 3.23 |
|  |  | 3.69457E−05 | 0.002035176 | nonAB* | 151 | −3.57 | 2.95 |
| SNP_A-2283283 | XKR4 | 0.000210491 | 0.006474865 | A_A* | 47 | −0.58 | 2.59 |
|  |  | 0.000210491 | 0.006474865 | A_B | 96 | −6.49 | 3.13 |
|  |  | 0.000210491 | 0.006474865 | B_B | 67 | −6.90 | 3.17 |
|  |  | 0.000210491 | 0.006474865 | nonAA** | 163 | −6.66 | 3.14 |
| SNP_A-4256833 | MLCK | 0.001705341 | 0.016306876 | A_A | 9 | −7.14 | 1.80 |
|  |  | 0.001705341 | 0.016306876 | A_B* | 64 | −2.62 | 3.36 |
|  |  | 0.001705341 | 0.016306876 | B_B | 137 | −6.45 | 3.14 |
|  |  | 0.001705341 | 0.016306876 | nonAB** | 146 | −6.49 | 3.08 |
| SNP_A-4258279 | RRM1 | 0.000310388 | 0.044200906 | A_A | 2 | −4.64 | 6.48 |
|  |  | 0.000310388 | 0.044200906 | A_B* | 45 | −0.66 | 3.01 |
|  |  | 0.000310388 | 0.044200906 | B_B | 160 | −6.29 | 2.93 |
|  |  | 0.000310388 | 0.044200906 | nonAB** | 162 | −6.27 | 2.96 |
| SNP_A-1819750 | CREG1 | 0.074338855 | 0.398903123 | A_A | 22 | −8.04 | 3.58 |
|  |  | 0.074338855 | 0.398903123 | A_B* | 119 | −4.58 | 3.12 |
|  |  | 0.074338855 | 0.398903123 | B_B | 46 | −6.81 | 3.21 |
|  |  | 0.074338855 | 0.398903123 | nonAB** | 68 | −7.21 | 3.35 |

TABLE 5-continued

SNPs associated with PANSS-GP score in iloperidone-treated patients

| SNP[1] | Gene[2] | Iloperidone[3] | Ilo vs. Pbo[4] | Genotype[5] | N[6] | Mean[6] | Std[6] |
|---|---|---|---|---|---|---|---|
| SNP_A-1860353 | RAP1B | 0.002845774 | 0.012178225 | A_A** | 5 | −17.20 | 2.97 |
|  |  | 0.002845774 | 0.012178225 | A_B | 35 | −5.17 | 2.99 |
|  |  | 0.002845774 | 0.012178225 | B_B | 169 | −4.96 | 2.88 |
|  |  | 0.002845774 | 0.012178225 | nonAA* | 204 | −5.00 | 2.90 |
| SNP_A-1975928 | SLC2A9 | 0.000154655 | 0.026316868 | A_A | 150 | −5.82 | 3.09 |
|  |  | 0.000154655 | 0.026316868 | A_B | 48 | −5.39 | 2.99 |
|  |  | 0.000154655 | 0.026316868 | B_B* | 6 | 9.62 | 4.95 |
|  |  | 0.000154655 | 0.026316868 | nonBB** | 198 | −5.72 | 3.06 |
| SNP_A-1987915 | GPR126 | 0.031457263 | 0.238695172 | A_A | 27 | −4.63 | 3.20 |
|  |  | 0.031457263 | 0.238695172 | A_B | 97 | −4.28 | 3.18 |
|  |  | 0.031457263 | 0.238695172 | B_B** | 85 | −7.14 | 3.13 |
|  |  | 0.031457263 | 0.238695172 | nonBB* | 124 | −4.36 | 3.17 |
| SNP_A-2007721 | LOC58486 | 8.90971E-05 | 0.001841909 | A_A | 1 | −2.52 |  |
|  |  | 8.90971E-05 | 0.001841909 | A_B** | 48 | −10.51 | 3.30 |
|  |  | 8.90971E-05 | 0.001841909 | B_B | 147 | −3.91 | 2.61 |
|  |  | 8.90971E-05 | 0.001841909 | nonAB* | 148 | −3.90 | 2.60 |
| SNP_A-2044214 | HNT | 0.015325757 | 0.040928723 | A_A | 86 | −6.83 | 3.61 |
|  |  | 0.015325757 | 0.040928723 | A_B* | 78 | −3.34 | 2.53 |
|  |  | 0.015325757 | 0.040928723 | B_B | 46 | −5.68 | 3.04 |
|  |  | 0.015325757 | 0.040928723 | nonAB** | 132 | −6.43 | 3.46 |
| SNP_A-2048427 | NPAS3 | 6.59322E-05 | 0.03604452 | A_A | 9 | −9.50 | 2.19 |
|  |  | 6.59322E-05 | 0.03604452 | A_B | 56 | −9.79 | 3.00 |
|  |  | 6.59322E-05 | 0.03604452 | B_B* | 145 | −3.44 | 2.83 |
|  |  | 6.59322E-05 | 0.03604452 | nonBB** | 65 | −9.75 | 2.89 |
| SNP_A-2274533 | LZTS1 | 0.000591957 | 0.012256756 | A_A** | 116 | −7.04 | 2.98 |
|  |  | 0.000591957 | 0.012256756 | A_B | 64 | −2.16 | 3.09 |
|  |  | 0.000591957 | 0.012256756 | B_B | 18 | −2.33 | 2.36 |
|  |  | 0.000591957 | 0.012256756 | nonAA* | 82 | −2.20 | 2.94 |
| SNP_A-2284243 | GRIA4 | 0.000147192 | 0.00611101 | A_A | 63 | −6.57 | 3.10 |
|  |  | 0.000147192 | 0.00611101 | A_B | 99 | −6.77 | 2.91 |
|  |  | 0.000147192 | 0.00611101 | B_B* | 48 | −0.77 | 3.12 |
|  |  | 0.000147192 | 0.00611101 | nonBB** | 162 | −6.69 | 2.98 |
| SNP_A-4204396 | CDH13 | 0.001744351 | 0.042910873 | A_A | 111 | −5.87 | 3.06 |
|  |  | 0.001744351 | 0.042910873 | A_B | 67 | −5.99 | 2.98 |
|  |  | 0.001744351 | 0.042910873 | B_B* | 15 | 1.39 | 3.87 |
|  |  | 0.001744351 | 0.042910873 | nonBB** | 178 | −5.91 | 3.03 |
| SNP_A-4212785 | PPP1R3B | 4.17363E-06 | 0.040340673 | A_A* | 4 | 15.61 | 2.26 |
|  |  | 4.17363E-06 | 0.040340673 | A_B | 67 | −5.99 | 3.04 |
|  |  | 4.17363E-06 | 0.040340673 | B_B | 124 | −5.84 | 3.10 |
|  |  | 4.17363E-06 | 0.040340673 | nonAA** | 191 | −5.89 | 3.07 |
| SNP_A-4230979 | ASB3 | 6.83689E-06 | 0.000197511 | A_A | 26 | −1.74 | 2.44 |
|  |  | 6.83689E-06 | 0.000197511 | A_B | 98 | −3.42 | 3.20 |
|  |  | 6.83689E-06 | 0.000197511 | B_B** | 85 | −8.85 | 3.05 |
|  |  | 6.83689E-06 | 0.000197511 | nonBB* | 124 | −3.07 | 3.12 |

[1]SNPs are identified by their Affymetrix SNP nomenclature (SNP_A-)
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]p value of the MMRM analysis between the 2 genotype classes associated with lowest * or highest ** response to iloperidone treatment
[4]p value of the MMRM analysis between the iloperidone (Ilo) and placebo (Pbo) groups for the genotype class associated with the better response (**).
[5]The 2 genotypes classes used in the MMRM analyses are indicated as associated with lowest * or highest ** response to iloperidone treatment.
[6]The number of patients (N), the mean of change in PANSS-GP (Mean), and the standard deviation of the mean (Std) shown here are derived from the MMRM analysis done within the group of iloperidone-treated patients.

TABLE 6

Odds ratio, sensitivity, specificity, and predictive values of SNPs associated with change in PANSS-T in iloperidone-treated group

| SNP[1] | Gene[1] | Genotype[3] | Delta-T ≥ −13[4] | | Delta-T < −13[4] | | Odds Ratio | P | 95% Confidence Interval | Sensitivity | Specificity | PV−[5] | PV+[6] |
|---|---|---|---|---|---|---|---|---|---|---|---|---|---|
|  |  |  | −test | +test | −test | +test |  |  |  |  |  |  |  |
| SNP_A-2048427 | NPAS3 | non-GG | 94 | 25 | 51 | 40 | 2.93 | 0.0005 | 1.596-5.388 | 0.44 | 0.79 | 0.65 | 0.62 |
| SNP_A-2283283 | XKR4 | non-GG | 35 | 84 | 12 | 79 | 2.82 | 0.0053 | 1.359-5.835 | 0.87 | 0.29 | 0.74 | 0.48 |
| SNP_A-1973093 | KIAA0040 | non-AG | 55 | 61 | 21 | 69 | 3.10 | 0.0003 | 1.671-5.744 | 0.77 | 0.47 | 0.72 | 0.53 |
| SNP_A-2274533 | GRIA4 | non-TT | 36 | 83 | 12 | 79 | 2.97 | 0.0035 | 1.431-6.148 | 0.87 | 0.30 | 0.75 | 0.49 |

TABLE 6-continued

Odds ratio, sensitivity, specificity, and predictive values of SNPs associated with change in PANSS-T in iloperidone-treated group

| SNP[1] | Gene[1] | Genotype[3] | Delta-T ≥ −13[4] | | Delta-T < −13[4] | | Odds Ratio | P | 95% Confidence Interval | Sensitivity | Specificity | PV−[5] | PV+[6] |
|---|---|---|---|---|---|---|---|---|---|---|---|---|---|
| | | | −test | +test | −test | +test | | | | | | | |
| SNP_A-2284243 | LZTS1 | AA | 60 | 54 | 22 | 62 | 3.16 | 0.0002 | 1.715-5.832 | 0.74 | 0.53 | 0.73 | 0.53 |
| SNP_A-2076797 | NUDT9P1 | GT | 77 | 41 | 32 | 58 | 3.48 | <0.0001 | 1.946-6.211 | 0.64 | 0.65 | 0.71 | 0.59 |

[1]SNPs are identified by their Affymetrix SNP nomenclature (SNP_A-)
[2]The gene name corresponds to the NCBI official symbol of the gene associated with the SNP as annotated by Affymetrix. Note that when a SNP is associated with more than one gene, the name of only the first gene in the annotation is listed. The SNP could be within or nearby the gene listed, or another gene in the same chromosomal region.
[3]The genotype class shown here is the genotype class associated with better efficacy to iloperidone treatment.
[4]The number of patients with change in PANSS-T (Delta-T) above and below −13 is shown per genotype class. This threshold was chosen to calculate values of a test predicting ~20% improvement of the mean: the mean Delta-T value (−11) was calculated from the LOCF data within the iloperidone group and was chosen as the threshold for all calculations. The genetic test was defined as positive (+) for the genotype class specified [3] associated with better response, and negative (−) for all other genotypes.
[5]Predictive value negative (PV−)
[6]Predictive value positive (PV+).

Many SNPs are not known to contribute directly to a particular phenotype, but may be physically linked on the same chromosomal region to other functional polymorphisms which do contribute directly to a particular phenotype. Accordingly, in addition to, or instead of, determining the genotype of a SNP itself, methods according to the present invention may include direct sequencing and/or the characterization of an expression product of a gene with which the SNP is associated. Such expression products include mRNA, peptides, and proteins.

The present invention also includes the prediction of an individual's response to treatment with iloperidone based on one or more of the SNP loci above in combination with the individual's genotype or gene sequence at one or more additional genes or loci. For example, International Patent Application Publication No. WO2006039663, incorporated herein by reference, describes a method of treating an individual with a compound capable of inducing QT prolongation based on the individual's CYP2D6 genotype. Other genes associated with QT prolongation include KCNQ1 and CERKL. Another gene associated with iloperidone efficacy is CNTF. These genes are merely illustrative of the additional SNPs and/or genotypes that may be used. Other genotypes and/or gene sequences may similarly be used in combination with the SNP loci above.

In addition, while the study above involved the administration of iloperidone (1-[4-[3-[4-(6-fluoro-1,2-benzisoxazol-3-yl)-1-piperidinyl]propoxy]-3-methoxyphenyl]ethanone), in some cases it may be advantageous to use iloperidone or an iloperidone metabolite preferentially in patients with certain genotypes as disclosed, e.g., in International Patent Application Publication No. WO2003054226, which is also incorporated herein by reference. Pharmaceutically-acceptable salts of iloperidone or iloperidone metabolites may also be used in the present invention.

Metabolites of iloperidone, e.g., P88 (also referred to as P-88-8891 or 1-[4-[3-[4-(6-fluoro-1,2-benzisoxazol-3-yl)-1-piperidinyl]propoxy]-3-methoxyphenyl]ethanol), are also useful in the present invention. See, e.g., International Patent Application Publication No. WO03020707, which is incorporated herein by reference. Other iloperidone metabolites include: 1-[4-[3-[4-(6-fluoro-1,2-benzisoxazol-3-yl)-1-piperidinyl]propoxy]-3-hydroxyphenyl]ethanone; 1-[4-[3-[4-(6-fluoro-1,2-benzisoxazol-3-yl)-1-piperidinyl]propoxy]-2-methoxyphenyl]-2-hydroxyethanone; 4-[3-[4-(6-fluoro-1,2-benzisoxazol-3-yl)-1-piperidinyl]propoxy]-3-hydroxy-_-methylbenzene methanol; 4-[3-[4-(6-fluoro-1,2-benzisoxazol-3-yl)-1-piperidinyl]propoxy]-2-hydroxy-5-methoxy-_-methylbenzenemethanol; 1-[4-[3-[4-(6-fluoro-1,2-benzisoxazol-3-yl)-1-piperidinyl]propoxy]-2-hydroxy-5-methoxyphenyl]ethanone; and 1-[4-[3-[4-(6-fluoro-1,2-benzisoxazol-3-yl)-1-piperidinyl]propoxy]-2,5-dihydroxyphenyl]ethanone. See U.S. Pat. No. 5,364,866, and International Patent Application Publication Nos. WO9309276 and WO9511680, which are incorporated herein by reference.

Iloperidone, an iloperidone metabolite, and/or pharmaceutically-acceptable salts thereof may be administered in any number of forms, including, for example, tablets, capsules, oral solutions, intravenous solutions, intramuscular injectables, intradermal injectables, suppositories, patches, inhalents, and nasal sprays. Similarly, such compounds may be provided in immediate release formulations, extended release formulations, or long-term injectable formulations (e.g., 28 day depot formulations). In addition, methods according to the invention may include once-, twice-, or thrice-daily administrations.

The present invention includes other aspects in addition to those described above. For example, in the case that an individual's SNP genotype(s), DNA sequence, and/or expression products are not associated with greater iloperidone efficacy, the individual may be administered an increased dose of iloperidone, an iloperidone metabolite, and/or pharmaceutically-acceptable salts thereof. In addition, the individual may be administered more frequent doses than would an individual having a SNP genotype, DNA sequence, or expression product associated with greater iloperidone efficacy. Alternatively, the individual may be administered a compound other than iloperidone, an iloperidone metabolite, or a pharmaceutically-acceptable salt thereof.

In another aspect, the invention comprises a kit for determining a SNP genotype or DNA sequence or for characterizing an expression product according to a method described above.

In another aspect, the invention comprises a method of selecting individuals for a drug trial, wherein individuals are selected for inclusion based on a predicted response to treatment with iloperidone, an iloperidone metabolite, and/or a pharmaceutically-acceptable salt thereof using one or more of the SNPs above, In another aspect, the invention comprises a method of analyzing results of a drug trial based on the patients' genotypes for one or more of the SNPs described herein.

In another aspect, the invention comprises screening and/or developing a composition having an increased or decreased efficacy in individuals of a particular genotype.

In another aspect, the invention includes a method of determining a genotype of an individual, the method including determining whether the individual possesses one or more SNPs above associated with greater iloperidone efficacy.

In yet another aspect, the invention includes a method of marketing iloperidone, an iloperidone metabolite, and/or pharmaceutically-acceptable salts thereof, the method including informing one or both of patients and pharmaceutical prescribers that individuals having one or more of the SNPs above associated with greater iloperidone efficacy are more likely to respond favorably to treatment with iloperidone, an iloperidone metabolite, and/or pharmaceutically-acceptable salts thereof.

The foregoing description of various aspects of the invention has been presented for purposes of illustration and description. It is not intended to be exhaustive or to limit the invention to the precise form disclosed, and modifications and variations are possible. Such modifications and variations that may be apparent to a person skilled in the art are intended to be included within the scope of the invention as defined by the accompanying claims.

What is claimed is:

1. A method of treating a human patient for one or more psychotic symptoms of using iloperidone, an iloperidone metabolite, or a pharmaceutically-acceptable salt of iloperidone or an iloperidone metabolite, the method comprising:
   determining, from a biological sample of the individual, the individual's genotype at the SNP_A-2048427 single nucleotide polymorphism (SNP) locus;
   determining, from a biological sample of the individual, the individual's genotype at the SNP_A-2274533 SNP;
   determining, from a biological sample of the individual, the individual's genotype at the SNP_A-2283283 SNP;
   in the case that the individual's genotype is determined to be non-GG at the SNP-A-2048427 SNP, AA at the SNP_A-2274533 SNP, and non-GG at the SNP-A-2283283 SNP, predicting that treating the individual with a daily dosage of 24 mg of iloperidone, an iloperidone metabolite, or a pharmaceutically-acceptable salt of iloperidone or an iloperidone metabolite will be efficacious and administering to the individual a daily dosage of 24 mg of iloperidone, an iloperidone metabolite, or a pharmaceutically-acceptable salt of iloperidone or an iloperidone metabolite; and
   in the case that the individual's genotype is determined to be GG at the SNP-A-2048427 SNP, non-AA at the SNP_A-2274533 SNP, or GG at the SNP-A-2283283 SNP, predicting that treating the individual with the daily dosage of 24 mg of iloperidone, an iloperidone metabolite, or a pharmaceutically-acceptable salt of iloperidone or an iloperidone metabolite will be less efficacious than treating the individual with a daily dosage greater than 24 mg and administering to the individual a daily dosage greater than 24 mg of iloperidone, an iloperidone metabolite, or a pharmaceutically-acceptable salt of iloperidone or an iloperidone metabolite.

2. The method of claim 1, wherein efficacious treatment includes improvement in at least one of the following: Positive and Negative Syndrome Scale total score (PANNS-T), Positive and Negative Syndrome Scale positive (PANNS-P) subscale score, Positive and Negative Syndrome Scale negative (PANNS-N) subscale score, or Positive and Negative Syndrome Scale general psychopathology (PANNS-GP) subscale score.

3. The method of claim 1, wherein determining includes sequencing of a gene containing the SNP_A-2048427 SNP locus, the SNP_A-2274533 SNP locus, or the SNP_A-2283283 SNP locus.

4. The method of claim 1, wherein determining includes:
   characterizing, from the biological sample, an expression product of a gene containing the SNP_A-2048427 single nucleotide polymorphism (SNP) locus, the SNP_A-2274533 SNP locus, or the SNP_A-2283283 SNP locus; and
   identifying the characterized expression product as associated with the non-GG genotype or the GG genotype at the SNP_A-2048427 SNP locus, with a non-AA genotype or the AA genotype at the SNP_A-2274533 SNP locus, and with the non-GG genotype or the GG genotype at the SNP_A-2283283 SNP locus.

5. A method of treating a psychotic symptom in a human individual, comprising:
   determining, from a biological sample of the individual, that the individual's genotype at the SNP_A-2048427 single nucleotide polymorphism (SNP) locus is non-GG;
   determining, from a biological sample of the individual, that the individual's genotype at the SNP_A-2274533 SNP is AA;
   determining, from a biological sample of the individual, that the individual's genotype at the SNP_A-2283283 SNP is non-GG; and
   administering to the individual a quantity of iloperidone.

6. The method of claim 5, wherein treating the psychotic symptom includes improving at least one of the following: Positive and Negative Syndrome Scale total score (PANNS-T), Positive and Negative Syndrome Scale positive (PANNS-P) subscale score, Positive and Negative Syndrome Scale negative (PANNS-N) subscale score, or Positive and Negative Syndrome Scale general psychopathology (PANNS-GP) subscale score.

7. The method of claim 5, wherein determining includes sequencing of a gene containing the SNP_A-2048427 SNP locus, the SNP_A-2274533 SNP locus, or the SNP_A-2283283 SNP locus.

8. The method of claim 5, wherein determining includes:
   characterizing an expression product of a gene containing the SNP_A-2048427 single nucleotide polymorphism (SNP) locus, the SNP_A-2274533 SNP locus, or the SNP_A-2283283 SNP locus; and
   identifying the characterized expression product as associated with the non-GG genotype or the GG genotype at the SNP_A-2048427 SNP locus, with a non-AA genotype or the AA genotype at the SNP_A-2274533 SNP locus, and with the non-GG genotype or the GG genotype at the SNP_A-2283283 SNP locus.

9. The method of claim 5, wherein the quantity of iloperidone is a daily dosage of 24 mg.

10. A method of treating a psychotic symptom in a human individual, comprising:
    determining that the individual's genotype at the SNP_A-2048427 SNP locus is GG, that the individual's genotype at the SNP_A-2274533 SNP locus is non-AA, or that the individual's genotype at the SNP_A-2283283 SNP locus is GG; and
    administering to the individual a quantity of iloperidone greater than would be administered to an individual having a non-GG genotype at the SNP_A-2048427 SNP locus an AA genotype at the SNP_A-2274533 SNP locus, or a non-GG genotype at the SNP_A-2283283 SNP locus.

11. The method of claim 10, wherein treating the psychotic symptom includes improving at least one of the following: Positive and Negative Syndrome Scale total score (PANNS-T), Positive and Negative Syndrome Scale positive (PANNS-P) subscale score, Positive and Negative Syndrome Scale negative (PANNS-N) subscale score, or Positive and Negative Syndrome Scale general psychopathology (PANNS-GP) subscale score.

12. The method of claim 10, wherein determining includes sequencing of a gene containing the SNP_A-2048427 SNP locus, the SNP_A-2274533 SNP locus, or the SNP_A-2283283 SNP locus.

13. The method of claim 10, wherein determining includes:
   characterizing an expression product of a gene containing the SNP_A-2048427 single nucleotide polymorphism (SNP) locus, the SNP_A-2274533 SNP locus, or the SNP_A-2283283 SNP locus; and
   identifying the characterized expression product as associated with the non-GG genotype or the GG genotype at the SNP_A-2048427 SNP locus, with a non-AA genotype or the AA genotype at the SNP_A-2274533 SNP locus, and with the non-GG genotype or the GG genotype at the SNP_A-2283283 SNP locus.

* * * * *